(12) United States Patent
Turck

(10) Patent No.: US 6,538,146 B2
(45) Date of Patent: Mar. 25, 2003

(54) METHOD FOR PRODUCING FATTY ACID ESTERS OF MONOVALENT ALKYL ALCOHOLS AND USE THEREOF

(75) Inventor: Ralf Turck, Mainstockheim (DE)

(73) Assignee: At Agrar-Technik GmbH, Schlaitdorf (DE)

( * ) Notice: Subject to any disclaimer, the term of this patent is extended or adjusted under 35 U.S.C. 154(b) by 0 days.

(21) Appl. No.: 10/012,811

(22) Filed: Dec. 7, 2001

(65) Prior Publication Data

US 2002/0156305 A1 Oct. 24, 2002

Related U.S. Application Data

(63) Continuation of application No. PCT/EP00/05255, filed on Jun. 7, 2000.

(30) Foreign Application Priority Data

Jun. 7, 1999 (DE) ............................... 199 25 871

(51) Int. Cl.[7] ................................................ C11C 3/10
(52) U.S. Cl. ...................... 554/169; 554/161; 554/163; 554/167; 554/168
(58) Field of Search ................................ 554/161, 163, 554/167, 168, 169

(56) References Cited

U.S. PATENT DOCUMENTS

| | | | |
|---|---|---|---|
| 5,354,878 A | | 10/1994 | Connemann et al. |
| 5,399,731 A | | 3/1995 | Wimmer |
| 5,434,279 A | * | 7/1995 | Wimmer ..................... 554/169 |
| 5,514,820 A | | 5/1996 | Assmann et al. |
| 5,849,939 A | | 12/1998 | Mittelbach et al. |

FOREIGN PATENT DOCUMENTS

| | | |
|---|---|---|
| AT | 386 222 B | 7/1988 |
| AT | 387 399 B | 1/1989 |
| AT | 397 966 B | 8/1994 |
| DE | 44 36 517 C1 | 10/1995 |
| EP | 0 131 991 B1 | 1/1985 |
| EP | 0 523 767 B1 | 1/1993 |
| GB | 2 051 786 A | 1/1981 |
| GB | 2 072 167 A | 9/1981 |

OTHER PUBLICATIONS

Kreutzer, et al., "Biodegradation of Nonionic Surfactants", JAOCS, vol. 61, No. 2 (Feb. 1984).

* cited by examiner

*Primary Examiner*—Deborah D. Carr
(74) *Attorney, Agent, or Firm*—Scully, Scott, Murphy & Presser

(57) ABSTRACT

The present invention relates to a method for producing fatty acid esters of monovalent alkyl alcohols by base-catalyzed transesterification of fatty acid esters of polyvalent alcohols. In said method, oils are used which contain free fatty acids and phosphatides, in addition to fatty acid esters of polyvalent alcohols. The method consists of several stages. The fatty acids contained in the starting material are treated with a base mixture of glycerine and a catalyst. This mixture is produced as a polar phase in the following transesterification stages and can be separated from the reaction mixture, using phase separation. Calculation procedures are provided for determining the minimum amount of catalyst necessary, depending on the acid number of the oil. The invention also relates to the use of esters produced by this method as diesel fuels.

20 Claims, 3 Drawing Sheets

METHOD FOR PRODUCING FATTY ACID ESTERS OF MONOVALENT ALKYL ALCOHOLS AND USE THEREOF

This is a continuation application of International Application No. PCT/EP00/05255 filed on Jun. 7, 2000.

BACKGROUND OF THE INVENTION

1. Technical Field

Fatty acid esters of monovalent alkyl alcohols are used in manifold applications both as raw material and as intermediate products in the chemical and pharmaceutical industries. Moreover, such compounds are also in the food-processing industry, too, and have also been employed particularly as Diesel fuels in the recent past.

2. Prior Art

For the production of these compounds various ways have been proposed, starting out from crude oil or reproducing raw materials. In practical application, a particular importance must be awarded to the preparation of such esters from vegetable or animal oils and fats, not least for reasons of protection of the environment. As a rule, the methods so far applied are based on the base-catalyzed transesterification of fatty acid esters of polyvalent alcohols, particularly of fatty acid glycerides (cf., for instance, *J. Am. Oil Chem. Soc.* 61 (1984), p. 343, or Ullmann, Encyclopedia of Industrial Chemistry, $4_{th}$ edition, vol. 11, page 432).

The industrial methods for the production of fatty acid esters of monovalent alkyl alcohols by base-catalyzed transesterification of fatty acid esters of polyvalent alcohols, which have been proposed in recent years, for instance those disclosed in the German Patent DE 3932514 or DE 4209779, employ partly a high expenditure in terms of apparatus and/or operate under cost-intensive conditions, i.e. at high temperatures and/or high pressures, and frequently also encompass complex processing steps such as distillations. For these reasons, such methods can be economically realized only at an industrial scale with quantities above 50,000 tons per year and more. These methods are not suitable for small installations producing 500 to 5,000 tons per year approximately. Methods specifically adapted to the potentials of such small installations are known, for example from the patents AT-386222, AT-397966, AT-387399, DE-3727981, DE-3020612, DE-3107318 or WO 92/00268. All of these methods are based on the aforementioned transesterification reaction and aim at a simplification going as far as possible, in an approach to reduce the costs and to permit an economic operation at a small scale as well. In particular, these methods try to desist from energy-intensive steps of separation, such as distillations, which are expensive and complex in terms of apparatus. Here the separation has been generally accepted as the established means of the first choice for the separation of the product or of intermediate products.

When non-refined starting oils are used, such as native oils, two important problems arise, however, with these methods. Native oils, specifically those of vegetable origin, contain, as a rule, slime substances such as phosphatides. These substances are surface-active and are therefore used partly as emulsifiers in the food-processing industry. In relation to the methods outlined here for the production of fatty acid esters, this characteristic furnishes the problem that these compounds take an expedient influence on the phase separation. Accordingly, a smooth realization of the method requires the use of starting oils from which the slime has already been removed, or the adoption of additional operating steps which require, as a rule, also supplementary parts of the installation for a reduction of yield losses induced by the incomplete or slow separation of phases. Fairly high levels of slime substances and particularly phosphatides in the starting oil give therefore rise to higher costs in conventional methods.

Moreover, the aforementioned oils often require also rather substantial quantities of free fatty acids whose presence takes a negative influence as well. As a matter of fact, these substances as free acids react with the basic catalyst added for transesterification, with the formation of soap. As a consequence, one part of the catalyst is neutralized and is therefore no longer available for the transesterification reaction. As a solution to this problem, it is possible to neutralize and/or remove the free fatty acids prior to the transesterification step proper, or it is necessary, on the other hand, to add a correspondingly larger quantity of the basic catalyst (cf. WO 92/00268).

This approach, however, leads to the consequence that on account of the required increased catalyst quantity additional costs are incurred and that hence rather substantial quantities of soaps are formed in the reaction mixture. As these compounds present surface-active properties as well they render the phase separation more difficult and must be separated, which gives again rise to further additional costs.

The present invention is therefore based on the problem of providing a method for the production of fatty acid esters of monovalent alkyl alcohols, which is as simple and economic as possible, which involves the lowest demands on the starting oils possible and which ensures, at the same time, high yields.

SUMMARY OF THE INVENTION

This problem is solved by a method for producing fatty acid esters of monovalent alkyl alcohols by base-catalyzed transesterification of triglycerides from natural or synthetic oils and/or fats containing free fatty acids and phosphatides as interfering accompanying substances, wherein initially the oils and/or fats are processed with an immiscible basic glycerin phase so as to neutralize the free fatty acids and cause them to pass over into the glycerin phase, and then upon separation of the glycerin phase by means of monovalent alcohols, the triglycerides are subjected to transesterification, using a base as catalyst, to form fatty acid esters, characterized in that after separation of the fatty acid esters, the basic glycerin phase produced during transesterification of the triglycerides is used for processing the oils and/or fats for removal of the free fatty acids, with the minimum quantity of catalyst used being calculated, relative to 1,000 g of the oil to be processed, as a function of the acid number of the oil and the mean molar mass of the oil, in correspondence with the equations (I) to (III):

with an acid number satisfying the inequation (I)

$$SZ < (0.084 \text{ mol}/1{,}000 \text{ g of oil})^*M(KOH)^*Y \qquad (I)$$

in correspondence with equation (II)

$$\text{minimum quantity of cat}/1{,}000 \text{ g of oil}=0.088 \text{ mol}/100 \text{ g oil}^*Y \qquad (II)$$

or else in correspondence with equation (III)

$$\text{minimum quantity of cat}/1{,}000 \text{ g oil}=(SZ/M/KOH)^* (0.088/0.084) \qquad (III)$$

with
 Y=(880 g/mol)/(mean molar mass of the oil used) and
 SZ=acid number of the oil used [(g KOH)/(1,000 g of oil)].

BRIEF DESCRIPTION OF THE DRAWINGS

Preferred embodiments of the present invention will now be described by way of example only, with reference to the accompanying drawings in which.

DETAILED DESCRIPTION OF THE PREFERRED EMBODIMENTS OF THE INVENTION

Figure 1:
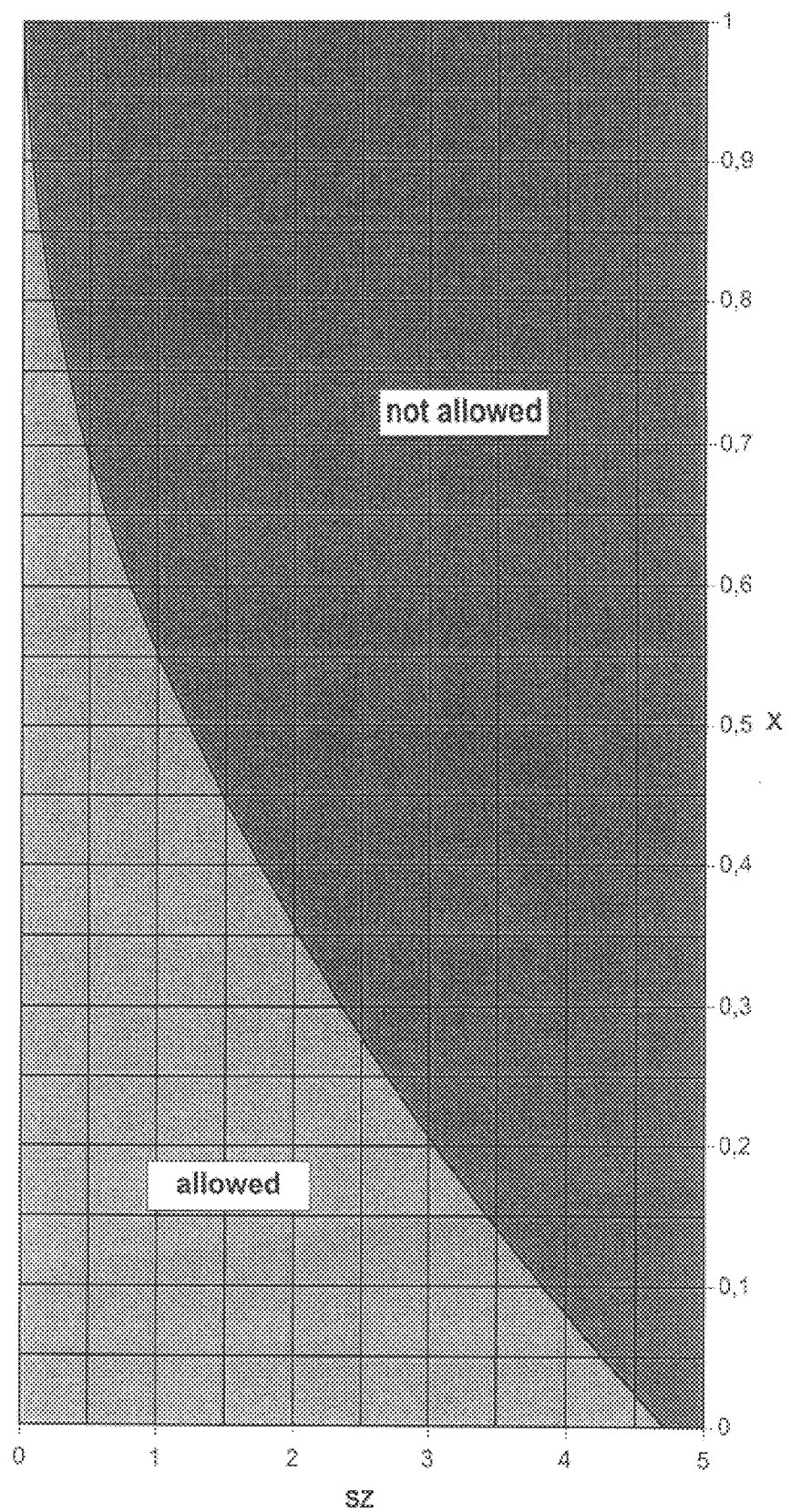
FIG. 1 is a schematic diagram illustrating a method in accordance with the present invention.

The inventive method is explained in more details by FIG. 1. The achieved advantages reside particularly in the aspect that starting oils having a high level of free fatty acids, which may also contain additional slime substances, can be processed without any problems to produce fatty acid esters of monovalent alkyl alcohols. Moreover, the inventive method requires only catalytic quantities of the base so that additional expenditures for catalyst material for the neutralization of the free acids are not incurred, as a rule, because the catalyst quantity produced during the transesterification step is available in the extraction step for the step of neutralization. Despite these simplifications, the inventive method furnishes a product of high purity and with a very good yield. The use of the basic glycerin phase, which is produced in the transesterification step and can be separated as polar and higher-weight phase and which contains substantially glycerin and the basic catalyst, in the neutralization step entails the particular advantage that additional impurities are not introduced along with a new base in the neutralization step.

In the inventive method triglycerides of any origin whatsoever can be processed as starting material. As an example, animal or vegetable fats and oils should be mentioned here, such as those conventionally used for the production of fatty acid esters. Colza or rapeseed oil is a particularly preferred starting material.

It was a surprise to find that the basic glycerin phase originating from transesterification is an excellent material suitable for the extraction of the free fatty acids from the starting material in a pre-processing step. The chemical substance active in this step is the alkaline transesterification catalyst that dissolves the free non-polar fatty acids in the form of ionic soaps in polar glycerin in this reaction step. Insofar, the catalyst is first used in the transesterification step and subsequently in the steps of neutralization and extraction of the free fatty acids.

The advantages achieved in correspondence with the invention reside particularly in the aspect that starting oils containing a high level of free fatty acids can be processed without any problems and with the least yield losses to produce fatty acid esters of monovalent alkyl alcohols. Apart therefrom, a previous removal of slime from the vegetable oils, which is required in other methods, is not necessary here.

In accordance with the present invention, the starting material is stirred with a basic glycerin phase in the first step of the method. In this step, the free fatty acids and residual water are largely extracted.

For this pre-processing step, the starting material is mixed with the basic glycerin phase for 1 to 60 minutes, preferably 5 to 15 minutes, preferably using an agitator vessel.

Only the setting or solidification point of the raw material limits the reaction conditions in this pre-processing step. In view of the economic aspect, this should carried out at ambient temperature and ambient pressure, in the case of higher solidification points at roughly 10° C. above this point and at ambient pressure.

The selection of the basic glycerin phase is variable. It must only be ensured that at least such a quantity of free catalyst is still available that all free fatty acids can be neutralized. As a rule, the fraction of free catalyst from the basic glycerin phase deriving from transesterification is also sufficient for raw materials presenting a high fraction of free fatty acids. The basic glycerin phase has a glycerin level of 20 to 99%, preferably 40 to 60%. The catalyst level ranges between 1 and 30%, preferably 5 and 10%. The fraction of the transesterification alcohol ranges between 5 and 40%, preferably 15 and 25%. Whenever this will be necessary, the basic glycerin phase can be supplemented also by the addition of a solid alkaline catalyst or an alcohol/catalyst mixture. Mixing glycerins of different qualities, from industrial to pharmaceutical qualities, and an alkaline catalyst with or without alcohols directly can also produce the agent used for glycerin extraction. All catalysts used for transesterification reactions, metal hydroxides and/or alcoholates particularly of metals from the main groups I to III of the periodic table, preferably NaOH, KOH and sodium alcoholates such as sodium ethylate, come into question as alkaline catalyst.

After the aforedescribed extraction step the reaction mixture can be separated by plain sedimentation and then be subjected to transesterification immediately. Usual sedimentation periods range between 15 minutes and 72 hours, preferably between 1 and 3 hours. The temperature of the raw material should be higher than the solidification point. In the case of vegetable oils such as rapeseed, soybean and sunflower oil an ambient temperature of 20° C. is sufficient, in the case of fats from animal bodies and deep fat fryer fats temperatures between 40 and 50° C. are realistic. The sedimentation temperature should generally range between 9 and 100° C., preferably between 20 and 40° C.

For an optimization of the utilization of the raw materials the idea offers itself, by the way, to separate the free fatty acids or their salts contained in the basic glycerin phase in accordance with document WO 95/02661 and to subject them to esterification with alkyl alcohol. This is preferably done with an acid catalysis. The reaction mixture obtained from this acid post-esterification can then be added to the transesterification mixture described in the following passages, by the end of the transesterification reaction. In such an approach one should note, however, that the acid catalyst neutralizes one part of the basic catalyst required for the transesterification. After completion of the pre-processing step the triglyceride contained in the material can be directly mixed with the base for carrying out the step of transesterification of the fatty acid esters of polyvalent alcohols to produce fatty acid esters of monovalent alkyl alcohols. %To this end, the mixture is passed into an agitator vessel.

The quantity of alkyl alcohol, which is used for transesterification, is distributed 1 to 10, preferably 2, transesterification stages. Altogether, roughly 1.05 to 2 mol of alcohol per mol of bound fatty acid fractions, preferably 1.2 to 1.4 mol, are used for the inventive method. With the usual two-stage realization of the method 40 to 99%, preferably 90 to 95%, are used in the first stage, and 1 to 60%, preferably 5 to 10%, are used in the second stage. The kind of the alkyl alcohol to be used is not subject to further limitations in the present method. However, linear, ramified or cyclic alkyl alcohols with 1 to 10 carbon atoms are preferred, with methanol being particularly preferable.

The base catalyzing the transesterification reaction, which may expediently be a metal hydroxide and/or a metal alcoholate, particularly of metals from the main groups I to III of the periodic table, may be added to the reaction mixture both in a solid form and in the form of an alcoholic solution. Potassium hydroxide is particularly preferred as base.

If an alcoholic solution is used such solutions are preferred which contain 25 to 50% by weight of the base, relative to the total weight of the solution. The alcohol quantity introduced in this manner must, of course, be included into the total alcohol quantity. The total quantity of the base, which is added in this step of the method, depends, in its turn, on the further development of the method and on the nature of the starting material. In the case of a single-stage transesterification, the total quantity of basic transesterification catalyst is used, of course, in this stage whereas in the case of a two-stage transesterification only 20 to 95%, and preferably 80 to 90%, of the total quantity are used.

The minimum quantity of the basic transesterification catalyst is determined by the transesterification process n the case of a low level of free fatty acids (low acid number; inequation (I) is satisfied) and can be determined in correspondence with equation (II). With higher acid numbers (inequation (I) is not satisfied) the neutralization of the free fatty acids becomes the determining step in the calculation of the required quantity of the catalyst. In such a case the minimum quantity of the base, which is to be used, can be determined by the equation (III). The numerical value 0.088 mol/1,000 g of oil is an empirically established mean value that had been determined in a way that an acceptable reaction speed will be ensured. 0.084 mol/1,000 g of oil out of this quantity are available for neutralizing the free fatty acids; the ratio 0.084/0.088 can hence be interpreted as re-cycling yield.

From an economic viewpoint, it is hardly sensible to exceed the theoretically calculated minimum quantity to be used by ten times. The use of 1 to four times the theoretically determined minimum quantity of basic transesterification catalyst to be used has turned out to be particularly expedient.

The reaction period in this stage corresponds to 5 to 60 minutes, and preferably to 25 to 35 minutes. As this stage, too, is realized preferably at ambient temperature and ambient pressure the precise reaction period must be matched with the respective conditions.

Figure 2:
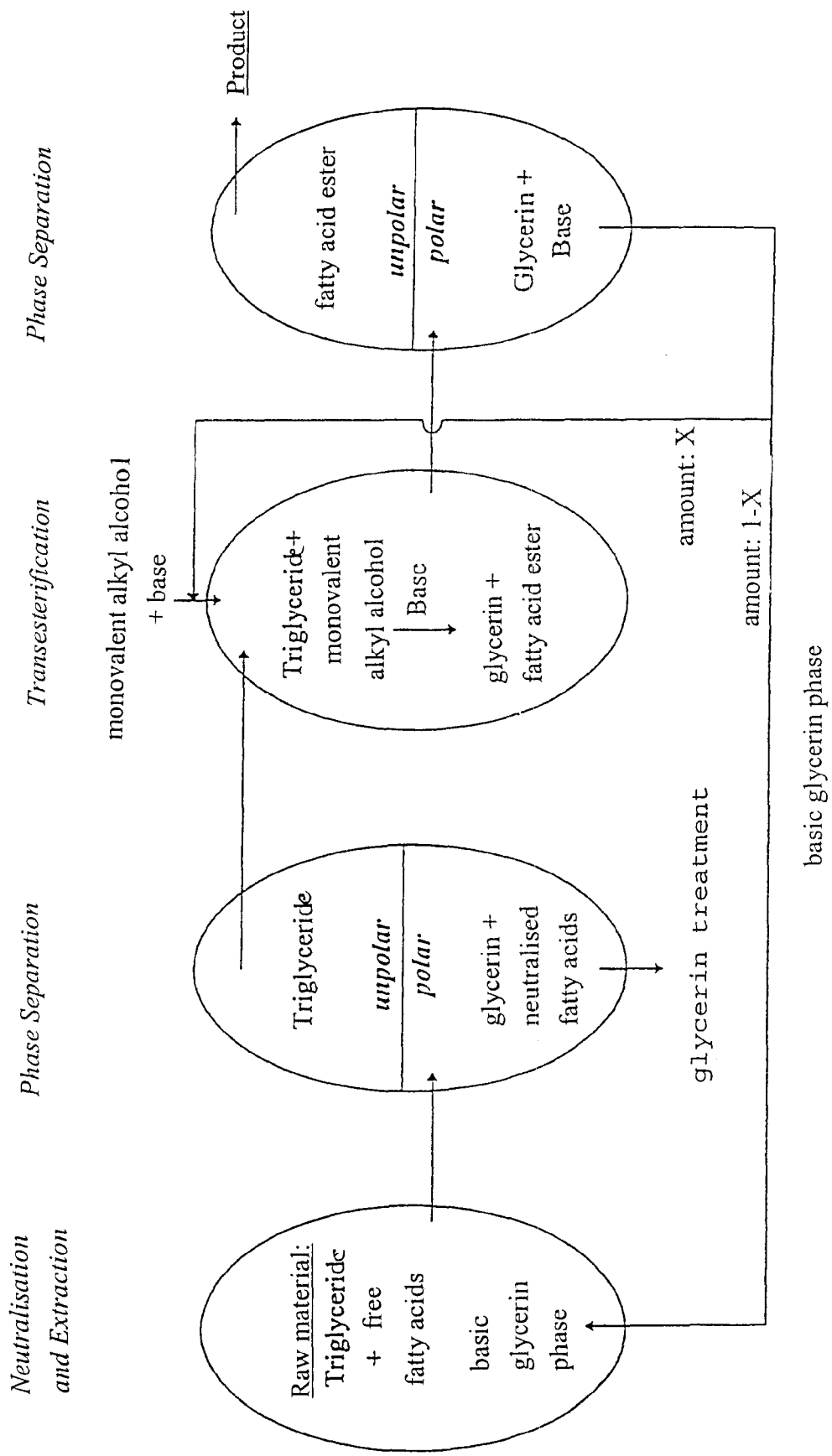
FIG. 2 is a schematic diagram illustrating an alternative method in accordance with the present invention.

In the case of low acid numbers in particular, a further reduction of the catalyst demand is possible when a fraction X of the glycerin phase produced during transesterification is re-used after separation of the fatty acid esters. This development of the method is schematically illustrated in FIG. 2.

Such a re-use of the basic glycerin phase is sensible only with an acid number satisfying the inequation (IV):

$$SZ < (0.084 \text{ mol}/1,000 \text{ g of oil})*M(KOH)*Y \quad (IV)$$

The minimum quantity of catalyst substance to be used (relative to 1,000 g of the oil to be processed) as well as the fraction X of the basic glycerin phase to be re-used for transesterification must be selected as a function of the acid number and the mean molar mass of the oil such that the equations (V) and (VI) will be satisfied at the same time:

minimum quantity of cat/1,000 g oil=(0.088 mol/1,000 g of oil–X*0.084 mol/1,000 g of oil))*Y (V)

minimum quantity of cat/1,000 g oil=$SZ/M(KOH)$*(0.088/0.084*(1–X)) (VI)

with $Y$=(880 g/mol)/(mean molar mass of the oil used)

$SZ$=acid number of the used oil [(g KOH)/(1,000 g of oil)]

$X$=fraction of the basic glycerin phase, which is re-used for transesterification.

Equation (V) corresponds to equation (II), the second term considers the re-used quantity of basic glycerin phase in the transesterification step. Equation (VI) is the corresponding match of equation (III). The required minimum quantity according to this equation is larger than the quantity determined by equation (III) because merely the fraction 1–X of the basic glycerin phase is used for neutralizing the free fatty acids. The re-use of the basic glycerin phase for transesterification reaches its limits where a sufficient quantity of the base for neutralizing the free fatty acids is no longer present in the fraction 1–X. Therefore, the optimum combination of the used base quantity and the re-use fraction X must be established with a simultaneous consideration of equation (VI) and equation (IV). With the equalization of equations (VI) and (VI) and with their transformation one can obtain a square equation whose single physically sensible solution furnishes a value of X in the range from 9 to 1. This maximum fraction X that can be used for transesterification may be used then in equations (V) or (VI) in the following for determining the required minimum quantity of the catalyst.

With the following substitutions:

$SZ/(M(KOH)*Y)=a$ 0.088 mol/1,000 g=b 0.084 mol/1,000 g=c the maximum fraction X sensible can be expressed by the following equation (VII):

$$X=(c^2+bc-((c^2+bc)^2-4bc^2*(c-a))^{0.5})/(2c^2) \quad (VII)$$

Figure 3:
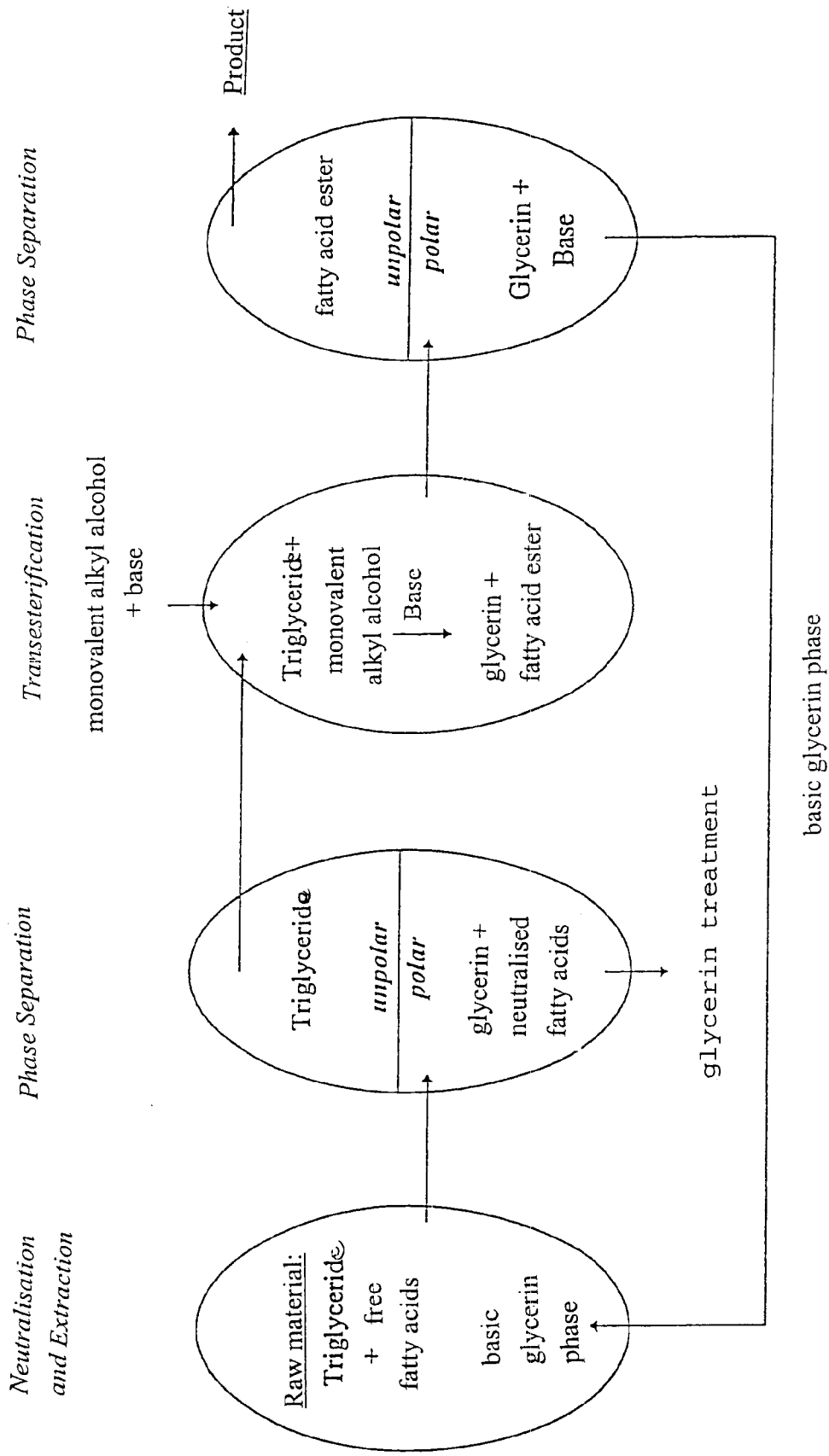
FIG. 3 is a graphical description of the fraction of the basic glycerin phase which is re-used for transesterification as a function of acid number of the used oil.

The re-use of smaller fractions of the basic glycerin phase for the transesterification is, of course, equally possible. This fact is graphically illustrated in FIG. 3 for a mean molar mass of the oil of 880 g/mol: fractions X within the range hatched slightly in FIG. 3 ensure a sufficient catalyst quantity in the remaining fraction (1–X) for the neutralization of the free fatty acids. After the aforedescribed transesterification stage the reaction mixture can be processed in a suitable manner, with the phase separation having turned out to be particularly expedient.

To this end, the mixture contained in the transesterification stage is supplied into a vessel that is expediently larger by a multiple than the reactor used for pre-processing and transesterification. The advantage of this dimensioning must be seen to reside in the fact that this settling vessel may be utilized as reservoir, with the result that, on the one hand, the settling periods may be longer than the time required for pre-processing and transesterification and that, on the other hand, a continuous removal of the product will be possible.

This vessel should furthermore be so designed that the resulting residual phase, which contains, inter alia, the polyvalent alcohols, and that the phase rich in fatty acid esters of monovalent alcohols can be extracted through two outlets mounted at two different locations.

The supply of the reaction mixture approximately at the level of the liquid/liquid phase boundary has turned out to be expedient, which can be achieved by an appropriately installed or configured inlet, as well as the removal of the ester-rich phase at the widest spacing possible from the phase boundary, which means that the outlet for the ester-rich phase should be installed as close as possible to the filling level limit of the vessel used for phase separation.

This optimization reaches, of course, its limit in the form of the fact that an outlet mounted at too high a location permits the removal of small quantities only whereas an outlet mounted farther down furnishes a product of reduced purity, even though the removal of larger quantities is possible. An expert for a given installation can easily determine the compromise that is required here. It is common to provide the outlet in the upper third of the vessel.

A phase rich in fatty acid esters of monovalent alkyl alcohol can be extracted from the vessel used for phase separation at a location above the liquid/liquid phase boundary and can be subsequently processed by conventional methods or even subjected to a second transesterification process.

A second transesterification process proposes itself always when the most complete transformation of the fatty acid residues contained in the starting product into fatty acid esters of monovalent alkyl alcohols is desired. To this end the separated phase is transferred into a second reactor, which is expediently designed as agitator vessel, and reacted with alkyl alcohol and the base under the same reaction conditions as in the first transesterification stage.

At this stage, alkyl alcohol must be added in a quantity of 5 to 80%, preferably 10 to 20%, of the total quantity given above, because the alkyl alcohol used in the previous steps migrates substantially into the glycerin phase during the step of phase separation.

The required alcohol quantity can be either added directly or mixed initially with the base and then supplied into the reactor. Here, too, one should expediently use the same alkyl alcohol or the same alkyl alcohol mixture as in the aforementioned stages.

Here, the same compounds as in the first transesterification stage come into question as the base, with alcoholic solutions of 25 to 50% by weight being preferred in view of easy handling.

The reaction time in this stage amounts to 15 to 45 minutes, preferably 25 to 35 minutes. The reaction mixture obtained after the second transesterification step, too, may be processed by one of the known methods, with the phase separation realized in one of the aforedescribed manners having turned out again as expedient. It is particularly advantageous to wash the reaction mixture with at least 5% of water, relative to the weight of the mixture containing fatty acids and used in this step before the last phase separation step.

It is moreover possible, after the last phase separation step, to expel low-boiling components from the fraction rich in fatty acid esters of monovalent alkyl alcohols. To this end, an evaporator is expediently used in which the fraction separated last is passed over a first surface heated to a temperature of 90 to 120° C. and the low-boiling components are deposited on a second surface.

The inventive method will be explained in more details in the following by examples and comparative examples.

COMPARATIVE EXAMPLE 1

500 g of a cold-pressed rapeseed oil with a level of 0.3% of free fatty acids (FFA level) are mixed, while stirring, with 52.5 g of methanol (99.7%) and 25 g of a 30% by wt. Solution of KOH (85%) in methanol in a Beaker at 293 K. After roughly 25 minutes, the agitator is stopped. The mixture is transferred into a separating funnel so that the two liquid phases can be collected in two vessels after roughly 3 hours. The biologic Diesel is completely transesterified by the addition of 2 g of a 30% solution of KOH in methanol and subsequently washed and dried. The yield is 495 g (99%) of rapeseed methyl ester and 82.5 g of basic glycerin phase of the following composition: approx. 65% of glycerin, approx. 18% of methanol, approx. 17% of free KOH and potash soaps.

COMPARATIVE EXAMPLES 2 to 5

The further comparative examples were realized in compliance with the directions for the Comparative Example. The relevant data of all Comparative Examples is compiled in Table 1.

TABLE 1

| Comparative Example | 1 | 2 | 3 | 4 | 5 |
|---|---|---|---|---|---|
| Used quantity [g] | 500 | 500 | 500 | 500,000 | 500 |
| type of fat | rape oil cold-pr. | rape oil cold-pr. | vegetable oil overacidified | deep-frying fat | animal body fat |
| FFA legal [%] | 0.3 | 1 | 3 | 5 | 9 |
| water content [%] | — | — | — | 1.9 | — |
| temperature [K] | 293 | 293 | 293 | 313 | 313 |
| added quantity of methanol (99.7%) [g] | 52.5 | 52.5 | 46.5 | 41,000 | 31.5 |
| added quantity of KOH (25.5%) in methanol [g] | 25 | 25 | 33.5 | 41,500 | 55 |
| period of phase separation [h] | 3 | 3 | 3 | 3 | 3 |
| 2. Transesterification: | | | | | |
| KOH (30%) in methanol [g] | 2 | 2 | 2 | 2,000 | 2 |
| Yield fatty acid methyl ester | | | | | |
| [g] | 495 | 480 | 440 | 400,000 | 300 |
| [%] | 99 | 96 | 88 | 80 | 60 |
| basic glycerin phase [g] | 82.5 | 97.5 | 140 | 182,500 | 286.5 |
| including [%] glycerin | 65 | 56 | 39 | 30 | 19 |
| [%] methanol | 18 | 15 | 11 | 8 | 5 |

TABLE 1-continued

| Comparative Example | 1 | 2 | 3 | 4 | 5 |
|---|---|---|---|---|---|
| [%] KOH (free and as potash soap) | 17 | 29 | 50 | 62 | 76 |

TABLE 2

| Comparative Example | 1 | 2 | 3 | 4 | 5 |
|---|---|---|---|---|---|
| Used quantity [g] | 500 | 500,000 | 500 | 500,000 | 500,000 |
| type of fat | rape oil cold-pr. | acid soy-bean oil | animal body oil | deep-frying fat | animal body fat |
| FFA level [%] | 1 | 4.3 | 9 | 5 | 12 |
| water content [%] | 0.2 | 0.35 | 0.8 | 1.9 | 1.2 |
| temperature [K] | 293 | 293 | 313 | 313 | 313 |
| added quantity of basic glycerin phase [g] | 50 | 50,000 | 50 | 50,000 | 75,000 |
| added quantity of KOH (25.5%) in methanol [g] | 25 | 25 | 33.5 | 41,500 | 55 |
| continued agitation [min] | 10 | 10 | 10 | 10 | 5 |
| Yield [g] | 495 | 478,000 | 450 | 465,000 | 433,000 |
| FFA level [%] | <0.1 | 0.3 | 0.3 | 0.2 | 0.3 |
| water content [%] | <0.1 | <0.1 | <0.1 | 0.1 | 0.1 |

TABLE 3

| Comparative Example | 1 | 2 | 3 | 4 | 5 |
|---|---|---|---|---|---|
| Used quantity [g] | 495 | 478,000 | | 465,000 | 433,000 |
| added quantity of methanol (99.7%) [g] | 59.3 | 52,600 | | 51,000 | 36,400 |
| added quantity of KOH (28.05%) in methanol [g] | 12 | 17,200 | | 16,800 | 29,000 |
| continuous agitation [min] | 25 | 25 | | 25 | 30 |
| period of phase separation [h] | 1 | 2 | | 3 | 3 |
| 2. Transesterification: | | | | | |
| KOH (33%) in methanol [g] | 3 | 4,300 | | 4,200 | 7,300 |
| Yield fatty acid methyl ester | | | | | |
| [g] | 492.5 | 473,000 | | 460,500 | 428,500 |
| [%] | 99.5 | 99 | | 99 | 99 |
| basic glycerin phase [g] | 73 | 79,100 | | 77,000 | 77,200 |
| including [%] glycerin | 68 | 60 | | 60 | 56 |
| [%] methanol | 20 | 18 | | 18 | 17 |
| [%] KOH (free) | 7 | 9 | | 9 | 15 |
| [%] KOH (as potash soap) | 4 | 7 | | 7 | 7 |
| [%] water | 1 | 6 | | 6 | 5 |
| total yield [%] | 98.5 | 94.6 | | 92.6 | 86.6 |

Example 1 (step a)

500 g of cold-pressed rapeseed oil with an FFA level of 1% and a water content of 0.2% are mixed, while stirring, with 50 g of basic glycerin phase (60% of glycerin, 20% of methanol, residue soaps and free KOH) in a Beaker at 293 K and subsequently intensively agitated for 10 minutes. The mixture is transferred into a separating funnel and finally the phases are separated by plain discharge after 3 hours of agitation. The yield amounted to 495 g at an FFA level and a water content of less than 0.1%.

Examples 2 to 5 (step a)

The fundamental approach corresponds to that of Example 1. All the pertinent data is compiled in Table 2.

Example 1 (step b)

The quantity of 495 g of cold-pressed rapeseed oil from Example 1 (step a) is mixed, while stirring, with 59.3 g of methanol (99.7%) and 12 g of a 33% by wt. Solution of KOH (85%) in methanol in a Beaker at 293 K. After 25 minutes approximately, the agitator is stopped and the mixture is transferred into a separating funnel. After roughly 1 hour, the two liquid phases are collected in two vessels. The biologic Diesel is completely transesterified into methanol by the addition of 3 g of a 33% of KOH in methanol, the glycerin phase so produced is separated and combined with the first one, and finally the biologic Diesel fuel is washed and dried. The yield amounts to 492.5 g (99.5%) of rapeseed methyl ester and 73 g of basic glycerin phase having the following composition: roughly 68% of glycerin, roughly 20% of methanol, roughly 4% of potash soaps, roughly 7% of free KOH and roughly 1% of water. The total yield, relative to the starting material prior to extraction, amounts to 98.5% approximately.

Examples 2 to 5 (step b)

The protocol of Example 1 (step b) was applied. The employed quantities, reaction conditions and yields are compiled in Table 3.

The comparison of the achieved yields in the Comparative Examples according to Table 1 against the total yields according to Table 3 reveals that the conventional method is able to compete with the present invention merely at a very low level of free fatty acids (Example 1 and Comparative Example 1).

The higher the level of free fatty acids in the employed starting material, the greater becomes the advantage of the present invention.

With an identical level of free fatty acids of 5% in Example 4 and in the Comparative Example 4, the total yield according to the method of the present invention, which amounts to 92.6%, is definitely higher than the yield achieved with the conventional method (80%).

The total yield of 86.6% for the transesterification of animal body fat according to the method of the present invention (Example 5) is substantially better than the yield obtained with conventional methods (60%; Comparative Example 5) that even with a higher fraction of free fatty acids (Example 5: 12% FFA level; Comparative Example 5: 9% FFA).

What is claimed is:

1. Method for producing fatty acid esters of monovalent alkyl alcohols by base-catalyzed transesterification of triglycerides from natural or synthetic oils and/or fats, which contain free fatty acids as interfering accompanying substances, wherein initially the oils and/or fats are processed with an immiscible basic glycerin phase so as to neutralize the free fatty acids and cause them to pass over into the glycerin phase, and subsequently, following separation of the glycerin phase by means of monovalent alcohols, the triglycerides are subjected to transesterification in an agitator vessel, using a base as a catalyst, to form said fatty acid esters, characterized in that following separation of the fatty acid esters, the basic glycerin phase, produced during transesterification of the triglycerides is used for processing the oils and/or fats for removal of the free fatty acids, with the minimum quantity of catalyst used being calculated, relative to 1,000 g of the oil to be processed, as a function of the acid number of the oil and the mean molar mass of the oil, according to the equations (I) to (III):

with an acid number satisfying the inequation (I)

$$SZ<(0.084 \text{ mol}/1{,}000 \text{ g of oil})*M(KOH)*Y \qquad (I)$$

according to equation (II)

$$\text{minimum quantity of cat}/1{,}000 \text{ g of oil}=0.088 \text{ mol}/100 \text{ g oil}*Y \qquad (II)$$

or else according to equation (III)

$$\text{minimum quantity of cat}/1{,}000 \text{ g oil}=(SZ/M/KOH)*(0.088/0.084) \qquad (III)$$

with $Y=(880 \text{ g/mol})/(\text{mean molar mass of the used oil})$ and
$SZ=$ acid number of the oil used $[(g \text{ KOH})/(1{,}000 \text{ g of oil})]$.

2. Method according to claim 1, wherein a base and an alkyl alcohol are added for transesterification to the triglycerides produced following said step of pre-processing with an immiscible basic glycerin phase, and wherein after transesterification, a fraction rich in fatty acid esters of monovalent alkyl alcohols is separated, with the fraction separated first, which is rich in fatty acid esters of monovalent alkyl alcohols, being mixed with a base and an alkyl alcohol for further transesterification and wherein, following transesterification, a second fraction rich in fatty acid esters of monovalent alcohols is separated.

3. Method according to claim 1, wherein metal hydroxides and/or alcoholates or their alkyl alcoholic solutions are used as the base.

4. Method according to claim 1, wherein the separation of said fractions rich in fatty acid esters of monovalent alkyl alcohols is carried out using phase separation.

5. Method according to claim 1, wherein, prior to the respectively last phase separation, the reaction mixture is washed with 5 or more % by weight of water, relative to the weight of the mixture containing fatty acid esters, which is used in this step.

6. Method according to claim 5, wherein low-boiling components are expelled from said fraction rich in fatty acid esters of monovalent alkyl alcohols following the respectively last phase separation.

7. Method according to claim 4, wherein a vessel is used for separating the fractions rich in fatty acid esters of monovalent alkyl alcohols, into which the respective starting mixture is supplied at or below the liquid/liquid phase boundary and from which the fraction to be separated is removed in the upper third of said vessel.

8. Method according to claim 6, wherein an evaporator is used to expel said low-boiling components, in which the fraction separated last is conducted over a first surface heated to between 90 and 120° C. and in which said low-boiling components are deposited on a second surface.

9. Method according to claim 1, wherein vegetable oils are used as a starting material.

10. Method according to claim 1, wherein alkyl alcohols containing 1 to 10 carbon atoms are used.

11. Method according to claim 1, wherein said step of pre-processing with said basic glycerin phase is carried out in an agitator vessel for a duration of between 1 and 60 minutes.

12. Method according to claim 11, wherein the duration of said pre-processing step is between 5 and 15 minutes.

13. Method according to claim 1, wherein 5 to 15% of the basic glycerin phase produced during transesterification are used in said pre-processing step.

14. Method according to claim 1, wherein, in addition to said basic glycerin phase produced during transesterification, additional glycerin and/or base is/are used for removing said free fatty acids.

15. Method according to claim 14, wherein additionally industrial glycerin or pharmaceutical glycerin is used, in which KOH, NaOH or sodium ethylate are dissolved.

16. Method according to claim 1, wherein the total quantity of basic transesterification catalyst used is between 1 and 4 times greater than the minimum quantity of catalyst according to claim 1.

17. Method according to claim 1, wherein the total quantity of alcohol used corresponds to between 1.2 and 1.4 mol per mol of bound fatty acid fractions.

18. Method according to claim 1, characterized in that a fraction X of said basic glycerin phase produced during transesterification of the triglycerides is re-used, following separation of said fatty acid esters, for the transesterification reaction, with the acid number satisfying the inequation (IV):

$$SZ<(0.084 \text{ mol}/1{,}000 \text{ g of oil})*M(KOH)*Y \qquad (IV)$$

and with the minimum quantity of catalyst to be used (relative to 1,000 g of the oil to be processed) as well as the fraction X of the basic glycerin phase to be re-used for transesterification being so selected that the equations (V) and (VI) are satisfied at the same time:

$$\text{minimum quantity of cat}/1{,}000 \text{ g oil}=(0.088 \text{ mol}/1{,}000 \text{ g of oil}-X*0.084 \text{ mol}/1{,}000 \text{ g of oil}))*Y \qquad (V)$$

$$\text{minimum quantity of cat}/1{,}000 \text{ g oil}=SZ/M/KOH)*(0.088/0.084*(1-X)) \qquad (VI)$$

with $Y=(880 \text{ g/mol})/(\text{mean molar mass of the used oil})$
$SZ=$ acid number of the used oil $[(g \text{ KOH})/(1{,}000 \text{ g of oil})]$
$X=$ fraction of the basic glycerin phase, which is re-used for transesterification.

19. Method according to claim 1, characterized in that the free fatty acids or their salts, respectively, which are separated using the basic glycerin phase, are subjected to post-esterification with alkyl alcohol.

20. Method of producing fuel for diesel engines, encompassing a method for producing fatty acid esters of monovalent alkyl alcohols according to claim 1.

* * * * *